(12) United States Patent
Fujita et al.

(10) Patent No.: US 7,625,088 B2
(45) Date of Patent: Dec. 1, 2009

(54) IMAGE PROCESSING APPARATUS

(75) Inventors: Hiroshi Fujita, Gifu (JP); Toshiaki Nakagawa, Gifu (JP); Takayoshi Suzuki, Hamamatsu (JP)

(73) Assignee: Kowa Company Ltd. (JP)

( * ) Notice: Subject to any disclaimer, the term of this patent is extended or adjusted under 35 U.S.C. 154(b) by 95 days.

(21) Appl. No.: 12/070,323

(22) Filed: Feb. 14, 2008

(65) Prior Publication Data
US 2008/0204656 A1 Aug. 28, 2008

(30) Foreign Application Priority Data
Feb. 22, 2007 (JP) .............................. 2007-041792
Jul. 17, 2007 (JP) .............................. 2007-185153

(51) Int. Cl.
*A61B 3/14* (2006.01)
(52) U.S. Cl. ....................... 351/206; 359/376; 351/240
(58) Field of Classification Search .................. 351/206
See application file for complete search history.

(56) References Cited

U.S. PATENT DOCUMENTS

| | | | | |
|---|---|---|---|---|
| 5,175,616 A | * | 12/1992 | Milgram et al. ............... | 348/47 |
| 5,815,314 A | * | 9/1998 | Sudo .......................... | 359/472 |
| 2007/0263923 A1 | * | 11/2007 | Gienko et al. ............... | 382/154 |
| 2009/0180072 A1 | * | 7/2009 | Suzuki ........................ | 351/207 |

* cited by examiner

Primary Examiner—Jessica T Stultz
(74) Attorney, Agent, or Firm—Adams & Wilks

(57) ABSTRACT

A model eye that models the optical characteristics of a human eye and is endowed with a grayscale pattern on the ocular fundus model surface is stereographically photographed with a parallax via a stereo photographic optical system. Photographed images are processed to provide calibration data for correcting the shape distortions of the stereo photographic optical system. The calibration data is used to correct a distortion-affected shape data and parallax images obtained in stereographic photography of the actual ocular fundus of a subject's eye. The shape distortion-corrected parallax image is used for a three-dimensional measurement process and 3D display on a stereo monitor. This allows an accurate three-dimensional measurement to be carried out and an accurate fundus image to be produced. The examiner can accurately evaluate the stereo shape of the ocular fundus of the subject's eye.

17 Claims, 12 Drawing Sheets

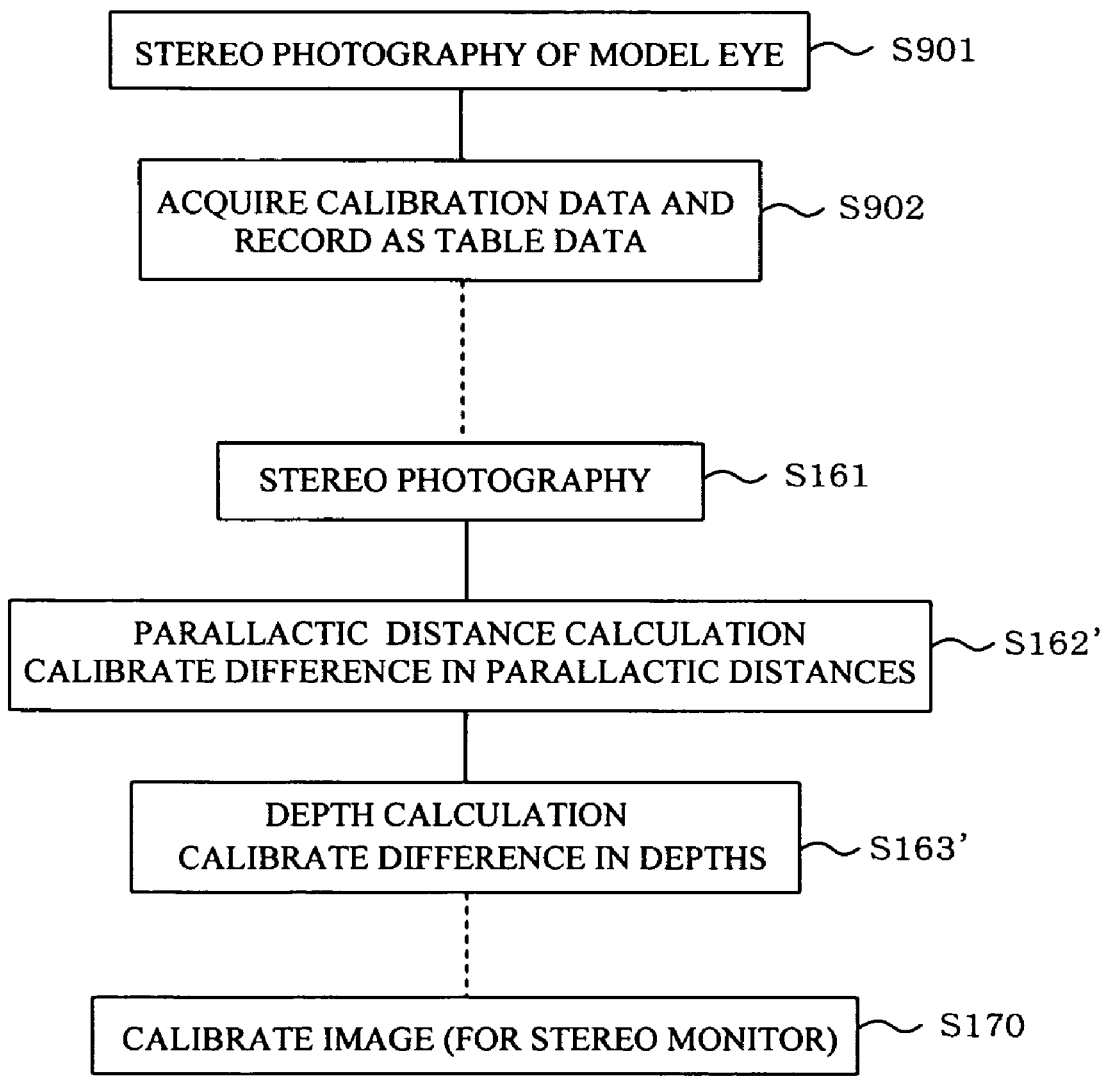

IMAGE PROCESSING APPARATUS

BACKGROUND OF THE INVENTION

1. Field of the Invention

The present invention relates to an image processing apparatus, and more particularly relates to an image processing apparatus for stereographically photographing the ocular fundus of a subject's eye with a prescribed parallax via an ocular fundus photographic optical system and for processing the resulting parallax images for three-dimensional shape measurement and three-dimensional display.

2. Description of the Prior Art

Conventionally known are a fundus camera and other image processing apparatuses for photographing a stereo image of the ocular fundus of a subject's eye in order to understand the shape of the ocular fundus of the subject's eye for the purpose of diagnosing glaucoma or performing other examinations. For example, an apparatus is known in which a photographic stop inside an optical system in a fundus camera is moved to different positions that are offset to the left and right (or up and down) from the optical axis to photograph the ocular fundus of the subject's eye at the offset stop positions, thereby providing stereographically viewed images (Japanese Laid-open Patent Application No. 1998-75932)

Image processing in which the ocular fundus is three-dimensionally measured can be carried out in the following manner. For example, the left and right (or upper and lower) images thus stereographically photographed are subjected to pattern matching in order to search corresponding points in both the images. If the corresponding points can be found, the basic principles of triangulation is used to calculate the coordinates along the z axis (the axis parallel to the optical axis) and the x and y axes (the two orthogonal axes that are parallel to the image surface) of an object point that is conjugate with the corresponding points. The three-dimensional coordinate values of a sufficient number of object points are calculated to produce a three-dimensional model of the ocular fundus of a subject's eye.

The left and right parallax images thus photographed are three-dimensionally displayed (3D display) via a 3D monitor or the like using various methods. In other words, the photographed left and right parallax images are independently presented to the left and right eyes of an observer (examiner). This allows the examiner to stereoscopically observe the state of the photographed ocular fundus of a subject's eye.

Image distortions are present in the optical system of a photography apparatus such as a fundus camera. For example, an image such as reference numeral 151 of FIG. 5 is photographed when a grid pattern such as graph paper placed on a flat surface is photographed. These distortions include those that are presumed to exist in advance in terms of the design of the optical system, as well as those that are produced by errors in manufacturing that vary depending on individual optical systems.

If stereographic photography and a three-dimensional image process are carried out in the manner described above using an optical system that has such image distortions, the z-axis coordinates obtained on the line P-P', for example, may possibly become deformed as shown by reference numeral 153 despite the fact that the z-axis coordinates should be linearly measured in the manner indicated by reference numeral 152 in the case of a grid pattern placed on a flat plane.

Generally, image distortions such as described above must be corrected in three-dimensional measurement in which a stereographically photographed image is used. Without correction a three-dimensional shape measured would be different than the actual photographic target. In view of this possibility, a configuration is used in which the image data is subjected to affine transformation using parameters that correspond to distortions of the optical system estimated in advance. In the case of ocular fundus photography, a configuration is known in which a stereographically photographed image is corrected under the presumption that the ocular fundus is an ideal sphere (Japanese Laid-open Patent Application No. 2002-34924).

However, it is difficult to say that such a conventional correction process accurately reflects the characteristics of the optical system used in actual photography, and it is highly possible that some type of error will occur in the three-dimensional measurement results of the ocular fundus. In clinical applications such as retinal shape analysis of the ocular fundus and papillary shape analysis of the optic nerve, there is risk of misdiagnosis depending on the extent of errors, and there is a need for an image process that can accurately correct for distortions in the optical system from the stereo photographic image.

For example, in the case of the grid pattern placed on a plane in FIG. 5, there is a need to be able to accurately correct in the manner of reference numeral 152 the three-dimensional shape on the line P-P' that has been distorted and measured as reference numeral 153.

It is believed that the shape data of the three-dimensional model of the ocular fundus of a subject's eye should be corrected in order to remove the effects of distortions in the optical system in this manner, and that the ocular fundus image thus photographed should be corrected. When left and right parallax images thus photographed are three-dimensionally displayed and the photographed ocular fundus of the subject's eye is stereographically presented to the examiner, it is preferred that the image also be corrected for 3D display so that the examiner can observe (perceive) the shape of the ocular fundus of the subject's eye by using the shape that reflects the correction of the shape data. When the photographed ocular fundus image is used for recording, i.e. printed on paper or the like, or recorded as data on an HDD or the like, it is naturally desirable that the image be corrected in the same manner.

It is therefore an object of the invention to provide an image processing apparatus for stereographically photographing the ocular fundus of a subject's eye and subjecting the resulting photographic image data to a three dimensional measuring process, wherein consideration is given to distortions in the optical system that is used in actual photography, an accurate three dimensional measuring process involving the fundus image can be performed, an accurate fundus image that corresponds to the three-dimensional measurement results can alternatively be provided, and the examiner can accurately evaluate the stereo shape of the ocular fundus of the subject's eye.

SUMMARY OF THE INVENTION

In accordance with the present invention, an image processing apparatus stereographically photographs an ocular fundus of a subject's eye with a prescribed parallax via an ocular fundus photographic optical system and performs a three-dimensional shape measurement process using the resulting parallax image. The apparatus comprises means for stereographically photographing a photographic target having a prescribed shape with a prescribed parallax via the ocular fundus photographic optical system; means for measuring the three-dimensional shape of a prescribed location of said target on the basis of image data derived from the parallax image thereof; and means for producing calibration data for correcting shape distortions caused by the ocular fundus photographic optical system, the calibration data corresponding to a difference between an actual three-dimensional shape of the prescribed location of said target and a three-dimensional shape of the prescribed location thereof that has been measured based on the image data.

In the invention, the calibration data is used in the three-dimensional shape measurement process for shape distortion correction for a three-dimensional shape data obtained by stereo photography of the ocular fundus of the subject's eye. Furthermore, the parallax image data obtained by stereo photography of the ocular fundus of the subject's eye is subjected to shape distortion correction based on the calibration data to produce shape distortion-corrected parallax image data of the ocular fundus of the subject's eye.

In particular, the photographic target may be a model eye that simulates the shape and optical characteristics of a human eye and has as a prescribed location an ocular fundus model surface endowed with a prescribed grayscale pattern.

The left and right parallax image data obtained by stereo photography of the ocular fundus of the subject's eye is subjected to shape distortion correction based on calibration data in order to produce left and right shape distortion-corrected parallax image data for stereo display on a stereo monitor.

In accordance with the configuration described above, distortions in an optical system used for actual photography are corrected, an accurate three-dimensional measurement process involving an ocular fundus image is performed, and/or an accurate ocular fundus image that corresponds to the three-dimensional measurement results can be provided in an image processing apparatus for stereographically photographing an ocular fundus of a subject's eye via an stereo photographic optical system and performing a three-dimensional shape measurement process based on the resulting photograph image data. Therefore, excellent effect is obtained in that the stereo shape of the ocular fundus of a subject's eye can be accurately evaluated and misdiagnoses and other problems can be avoided.

Also, calibration measurement and computation can be easily carried out without changing other photographic and computational conditions by using a model eye for modeling the shape and optical characteristics of a subject's eye.

An examiner can readily ascertain the state of the ocular fundus of the subject's eye via stereographic observation by producing left and right image data corrected based on the shape distortion correction and stereographically displaying the data using a stereo monitor.

Corrected image data can be produced in which the shape distortion correction has been applied to the parallax image data obtained by stereo photography of the ocular fundus of the subject's eye by geometric computation using the calibration data, which is expressed by the depth to be corrected in the three-dimensional measurement process. The correction image data can also be provided for displaying, recording, and other purposes.

Further features of the invention, its nature and various advantages will be more apparent from the accompanying drawings and following detailed description of the invention.

BRIEF DESCRIPTION OF THE DRAWINGS

FIG. 9 is a flowchart showing calibration and photographic processes in the apparatus of FIG. 1;

DESCRIPTION OF THE PREFERRED EMBODIMENTS

Described below is the present invention embodied as an ophthalmic measuring apparatus for producing a stereo photograph of the ocular fundus of a subject's eye via a stereo photographic optical system and processing the resulting photographic image data for three-dimensional measurement and display.

Figure 1:
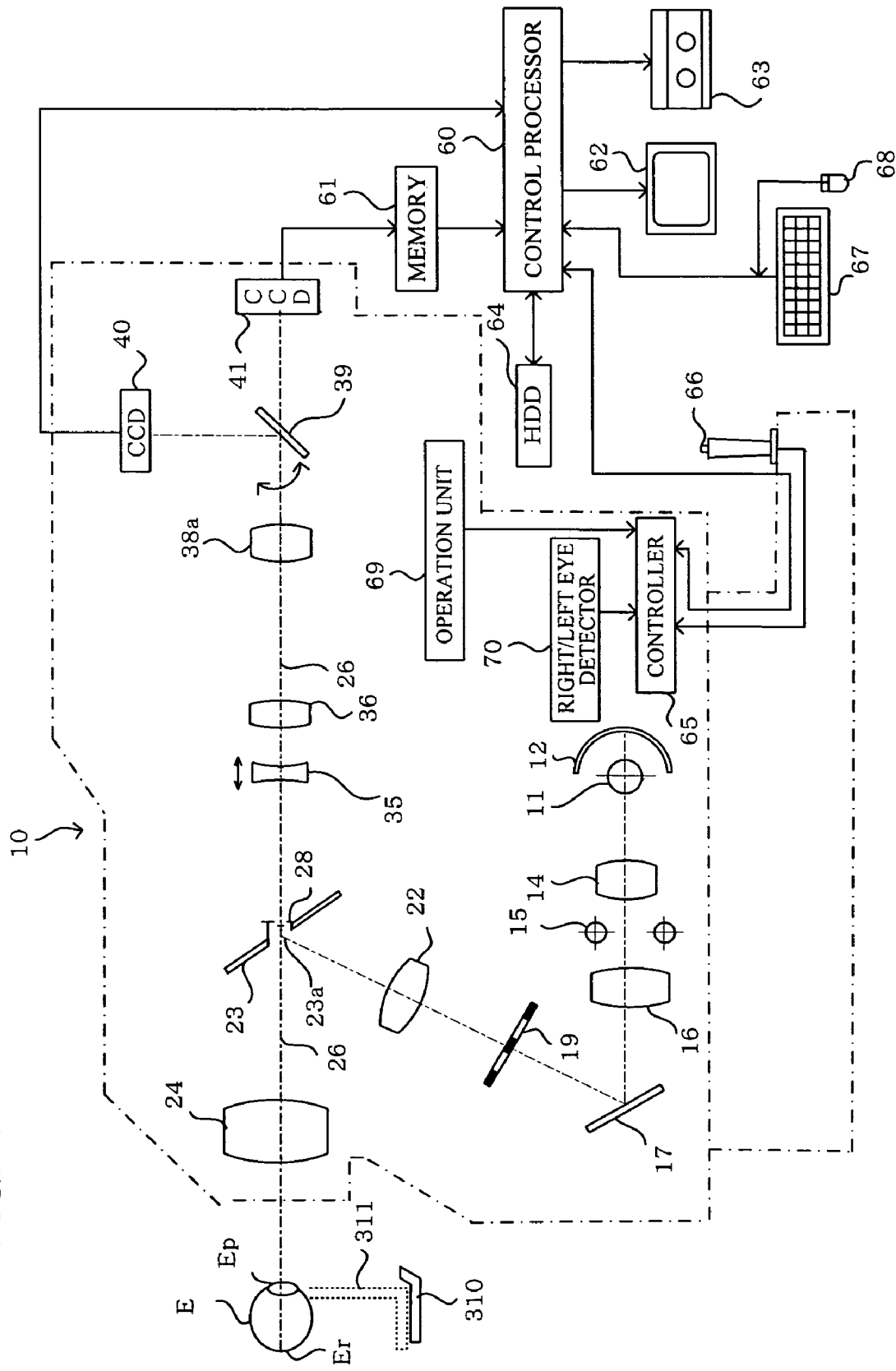
FIG. 1 is a schematic diagram showing the configuration of a fundus camera as an image processing apparatus according to the present invention.

In FIG. 1, a fundus camera 10 enclosed and depicted by the alternate long and short dash line is provided with an observation lamp 11 that emits infrared and visible illumination light and is disposed in the center of the curvature of a spherical mirror 12. The light from the observation lamp 11 and the spherical mirror 12 travels though a condenser lens 14, a strobe light 15 as a photographic light source, and a condenser lens 16, and is then incident on the total reflection mirror 17.

The illumination light reflected by the total reflection mirror 17 is transmitted through a relay lens 22 via an illumination stop 19, is reflected by an apertured total reflection mirror 23, and is incident on an anterior ocular segment (pupil) Ep of a subject's eye E via an objective lens 24. The illumination stop 19 is disposed in the illumination optical system at a position substantially conjugate with the anterior ocular segment Ep (pupil) of the subject's eye.

Reflected light from the eye fundus Er illuminated by illumination light is transmitted through the objective lens 24, an aperture 23a of the apertured total reflection mirror 23, an aperture of the two-apertured photographic stop 28, a focusing lens 35, an imaging lens 36, and a variable power lens 38a, and is incident on a return mirror 39. When the return mirror 39 is positioned as shown, light reflected from the ocular fundus is incident on an infrared light-sensitive CCD (imaging means) 40 that is in a position substantially conjugate with the ocular fundus to form an image of the ocular fundus. When the return mirror 39 is removed from the optical path, reflected light from the ocular fundus is incident on a visible light-sensitive CCD (imaging means) 41 that is in a position substantially conjugate with the ocular fundus to photograph an image thereof.

Figure 2A:
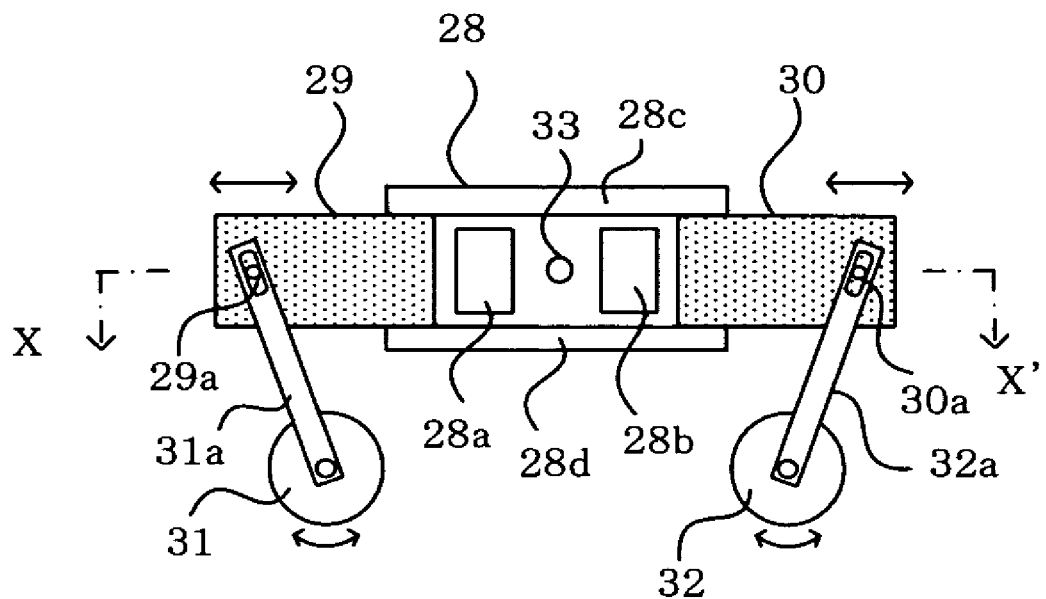
FIG. 2a is a front view showing the configuration of the area around the photographic stop of FIG. 1.
Figure 2B:
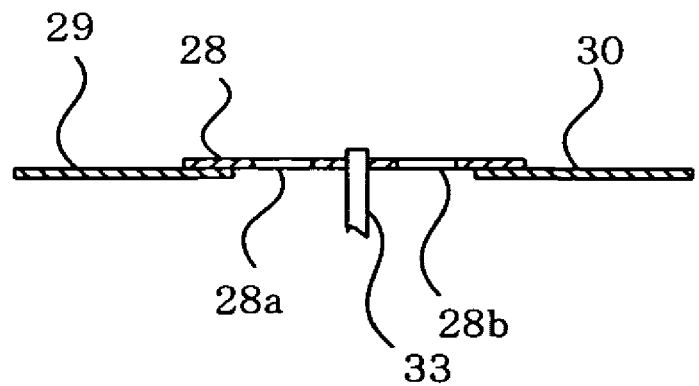
FIG. 2b is a top view showing the configuration of the area around the photographic stop of FIG. 1.

The photographic stop 28 is provided with two rectangular apertures 28a and 28b, as shown in FIGS. 2a and 2b. The apertures 28a and 28b of the photographic stop 28 are offset from the optical axis 26 and are disposed so as to be symmetrical relative thereto in substantially conjugate positions with the anterior ocular segment (pupil) of a subject's eye.

The size and position of the apertures 28a and 28b are set so that the aperture 23a of the apertured total reflection mirror 23 includes the entire set of apertures 28a and 28b.

The apertures 28a and 28b of the photographic stop 28 are opened or closed by shutter plates 29 and 30 that are moved along the guides 28c and 28d, respectively.

Switching means composed of rotary solenoids 31 and 32 are provided in order to achieve this opening and closing. When the rotary solenoids 31 and 32 are not energized, the shutter plates 29 and 30 are in the position shown in FIG. 2a to open the apertures 28a and 28b, respectively.

Conversely, when the rotary solenoids 31 and 32 are energized, rods 31a and 32a of the rotary solenoids 31 and 32 rotate and the other ends of the rods 31a and 32a engage pins 29a and 30a on the shutter plates 29 and 30. This causes the shutter plates 29 and 30 to be moved inward to close the apertures 28a and 28b.

The fundus image formed by the CCD 40 is inputted to a control processor 60 composed of a CPU and the like, and the video image is displayed on a monitor 62. An examiner views the image displayed on the monitor 62 and can make alignments, adjust the focus, and perform other operations described hereinafter. A stereo monitor 63 is provided as a display for dedicated stereographic viewing, and the examiner can stereographically view the ocular fundus by observing the left and right images via the stereo monitor 63.

Various methods are available for displaying images on the stereo monitor 63, including varying the polarization direction and display color between the left and right stereo images, and independently observing left and right stereo images via an observation scope that separates the left and right visual fields. However, the display method of the stereo monitor 63 of the present embodiment is arbitrary, and any stereo display method can be used as long as the configuration allows the left and right parallax images to be independently observed by the left and right eyes of the examiner.

The CCD 41 can photograph a still image of the ocular fundus illuminated by the strobe light 15 when a shutter switch 66 is operated. The image of the ocular fundus is temporarily stored in a high-speed memory 61 and is recorded via the control processor 60 in recording means, which is implemented using a low-speed hard disk (HDD) 64 as an external recording device, or is displayed on the monitor 62 or stereo monitor 63.

A keyboard 67, mouse 68, or other input means is also provided, and various data can be inputted via these input devices.

The controller 65 composed of a CPU or the like is provided to the fundus camera. The controller 65 is connected to the control processor 60 and exchanges signals with the processor. When the shutter switch 66 is operated, the controller 65 removes the return mirror 39 from the optical path and also causes the strobe light 15 to emit a suitable amount of light. The controller 65 additionally controls the insertion and removal of the variable power lens 38a and the like into and from the optical path, and also controls the driving of the rotary solenoids 31 and 32 described above.

An operation unit (operation panel) 69 is also provided to the fundus camera, and the operation unit 69 can be used to select a photography mode. A right/left eye detector 70 for detecting whether the subject's eye to be photographed is the left or right eye is furthermore provided, and information detected by the right/left eye detector 70 concerning whether the eye is the left or right eye is inputted to the controller 65.

An overview of stereoscopic photography of the ocular fundus of a subject's eye in the configuration described above will be described next.

First, the observation lamp 11 is turned on during observation and the illumination stop 19 is inserted into the optical path. The rotary solenoids 31 and 32 are driven to the positions shown in FIG. 2a, and the two apertures 28a and 28b of the photographic stop 28 are thereby set in the open position. The light reflected from the ocular fundus of the subject's eye illuminated by infrared light via the illumination stop 19 is captured in the CCD 40 for observation via the apertures 28a and 28b of the photographic stop 28, and an image of the ocular fundus is displayed on the monitor 62.

Alignment and focusing relative to the subject's eye are performed in this state. At this time, the alignment and focusing operations of the examiner are supported by a visual target projection system (not shown).

When alignment and focusing operations are completed, the examiner presses downward on the shutter switch 66. The controller 65 drives the rotary solenoid 31 and moves the shutter plate 29 in the rightward direction in response to the shutter switch operation to close the aperture 28a of the left side of the photographic stop 28. The strobe light 15 emits light in synchronization with the operation of the shutter switch 66, and the return mirror 39 is removed from the optical path. Therefore, the beam of light from the ocular fundus illuminated by the strobe light 15 is transmitted through the open aperture 28b of the photographic stop 28 and is incident of the image sensor surface of the CCD 41. A first ocular fundus image for stereoscopic viewing is captured by the CCD 41 as a still image and is stored in the memory 61.

The rotary solenoids 31 and 32 are subsequently controlled to move the shutter plates 29 and 30 in the left direction in order to open the aperture 28a and close the aperture 28b. The strobe light 15 is again made to emit light. At this time, a second ocular fundus image for stereographic viewing that has passed through the aperture 28a is captured by the CCD 41 as a still image and stored in the memory 61.

In this manner, photographs are sequentially taken from two viewpoints, i.e., the left and right viewpoints, with a single shutter operation. The two parallax images thus stereographically photographed are associated with the position of the opened aperture of the photographic stop, i.e., the left position, the right position, or other information, and saved from the memory 61 to an HDD 64. The two parallax images saved in this manner are read from the HDD 64, and are displayed using the stereo monitor 63. The examiner can stereographically view an ocular fundus image by observing the ocular fundus image that corresponds to the left or right eye.

Prior to describing the calibration process of the present invention, the processes will be described that are involved in measuring the stereographic shape of the ocular fundus of a subject's eye in three dimensions from the left and right parallax images stereographically photographed in the manner described above.

Figure 6:
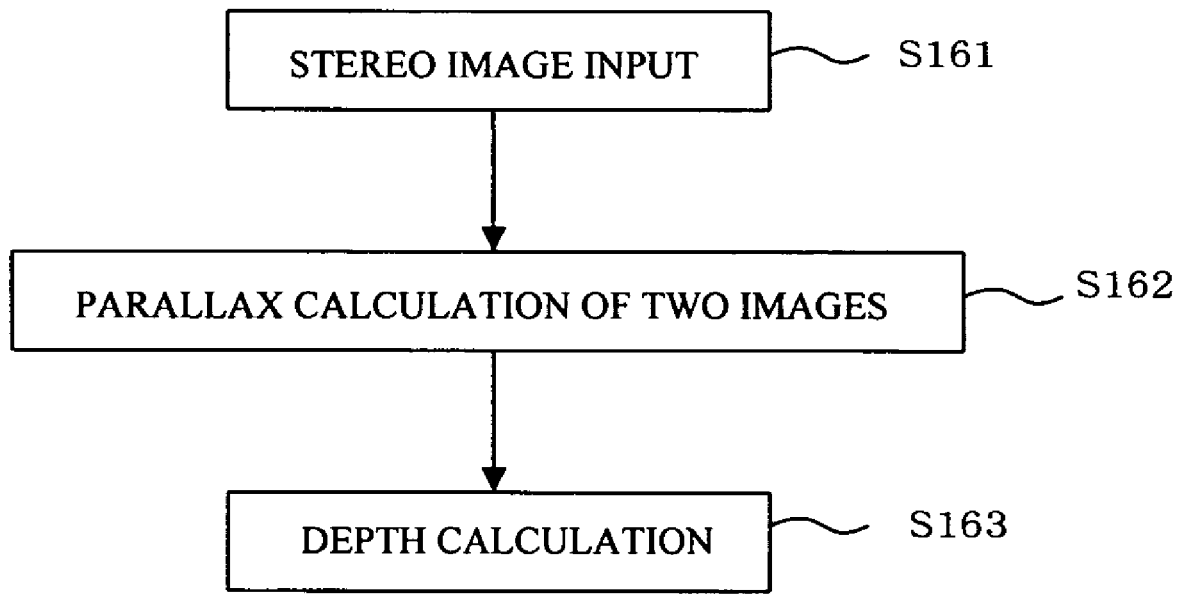
FIG. 6 is a flowchart showing a stereo photographic process and a three-dimensional measurement process in the apparatus of FIG. 1.

FIG. 6 is an overview of the three-dimensional measurement process involving the ocular fundus. In step S161 of FIG. 6, the ocular fundus of a subject's eye is stereographically photographed in the manner described above.

The parallactic distance between the left and right parallax images thus stereographically photographed is subsequently calculated in step S162. Parallactic distance calculation is performed in the following manner.

Figure 7:
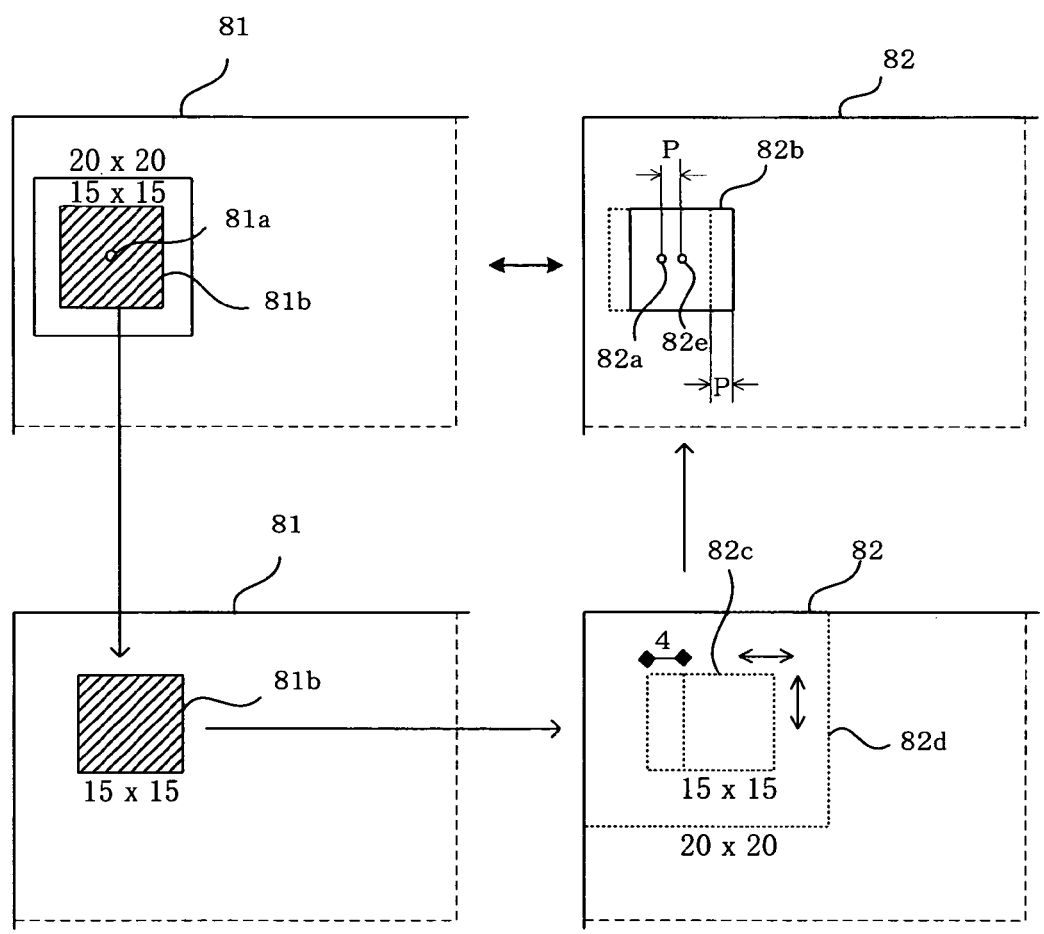
FIG. 7 is an illustrative view showing the manner in which parallactic distance measurements are processed in the apparatus of FIG. 1.

First, a 15×15 pixel area 81b of interest is set about the center of a point (pixel) 81a of attention for which the parallactic distance in the left parallax image 81 is to be calculated (FIG. 7). An area 82b having the highest correlation with the area 81b of interest of the left parallax image 81 is searched from inside the right parallax image 82 using pattern matching.

Since time is required to search the entire image, the search area is limited to a 20×20 pixel area 82d. In other words, a search is carried out in the range of a 20×20 pixel area 82d in the right parallax image 82 about the center of a point 82a therein that corresponds to the center of point 81a for which the parallactic distance of the left parallax image 81 will be calculated.

The point of attention for which the parallactic distance is to be calculated is set to be all of the points in the left parallax image 81, and for each point the area in which the highest correlation is achieved is searched in the right parallax image 82. For this search, the 15×15 pixel area 82c is shifted for every pixel, or every fourth pixel within the 20×20 pixel search area 82d in the right parallax image 82, as shown in lower right portion in FIG. 7.

The offset of the position of the area 82b in the right parallax image 82 having the highest correlation with respect to the area 81b of interest in the left parallax image 81 is calculated as parallax P (parallactic distance: the number of parallax pixels). The point 81a of attention in the left parallax image 81 corresponds to a point 82e located at the center of the area 82b in the right parallax image 82. In this manner, the parallactic distance P is calculated for each point of attention.

The process described above makes it possible to calculate the parallax (parallax pixel number) of a specific pixel corresponding to a specific location in the ocular fundus, i.e., to determine the number of pixels by which the specific location is offset in the photographed left and right parallax images.

A parallax pixel number of a specific pixel on the photographic screen or of a specific location on the ocular fundus can be transformed into the actual parallactic distance on the retina (ocular fundus) as long as the photographic power (or photographic distance) conditions of the optical system are known.

If the actual parallactic distance of a specific pixel or a specific location on the retina (ocular fundus) is measured, the depth (or the coordinate value in the z-axis direction parallel to the optical axis) of the specific pixel or the specific location can be calculated in the following manner (S163 of FIG. 6).

Figure 8:
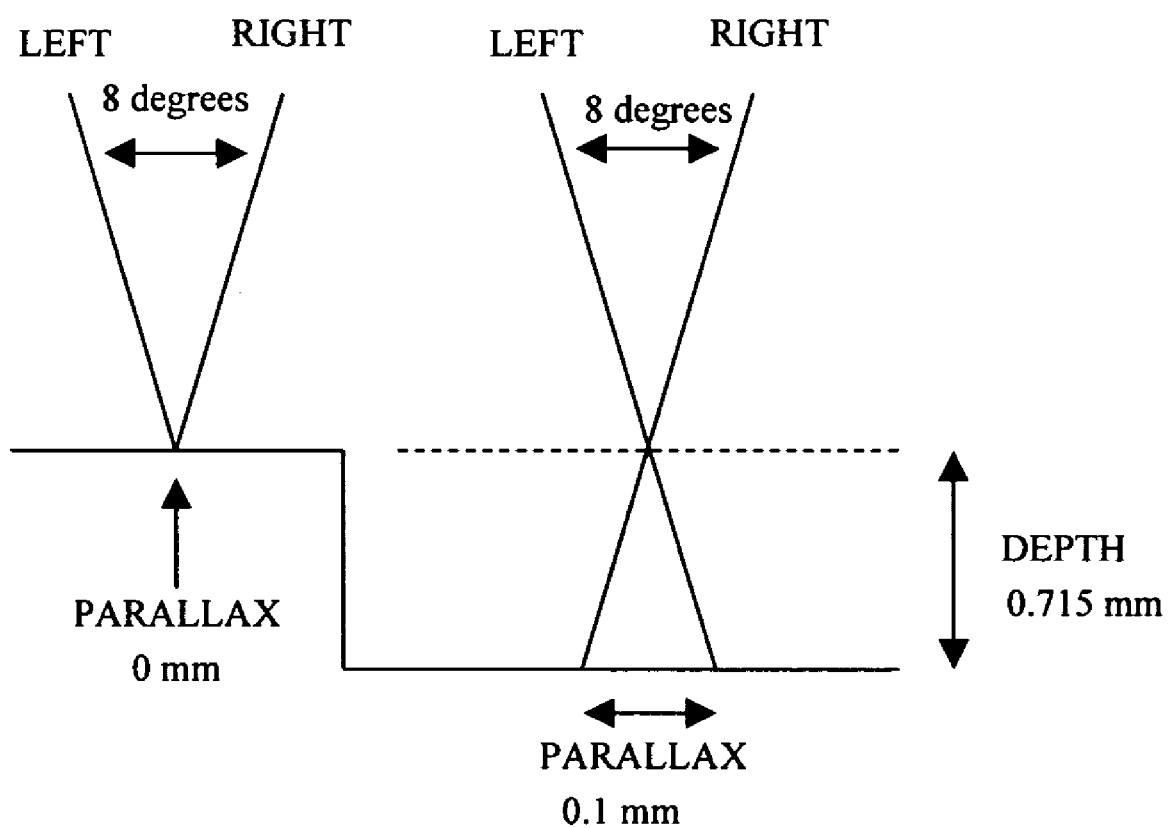
FIG. 8 is an illustrative view showing the manner in which depth (z-axis coordinate) is measured in the apparatus of FIG. 1.

When the parallactic angle determined by the photographic distance and the positions of the photographic stops 28a and 28b is assumed to be 8 degrees, for example, and the parallactic distance of a specific location on the ocular fundus is calculated to be 0.1 mm via the above-described computation (S162), the depth (length, or the coordinate in the z-axis direction) of the specific location thereof is calculated from the parallactic distance with the aid of the following formula to be 0.715 mm (relative distance from the location of parallactic distance 0) using the principle of triangulation as shown in FIG. 8.

$$\text{Depth} = (\text{Parallactic distance}/2)/\tan(\text{Parallactic angle}/2) \quad (1)$$

In the case of a fundus camera, the photographic distance is adjusted to a working distance by alignment prior to photographing. For this reason, a three-dimensional measurement process may be carried out on the assumption that the parallactic angle (8 degrees in the example above) determined by the position of the stops 28a and 28b is constant.

Figure 5:
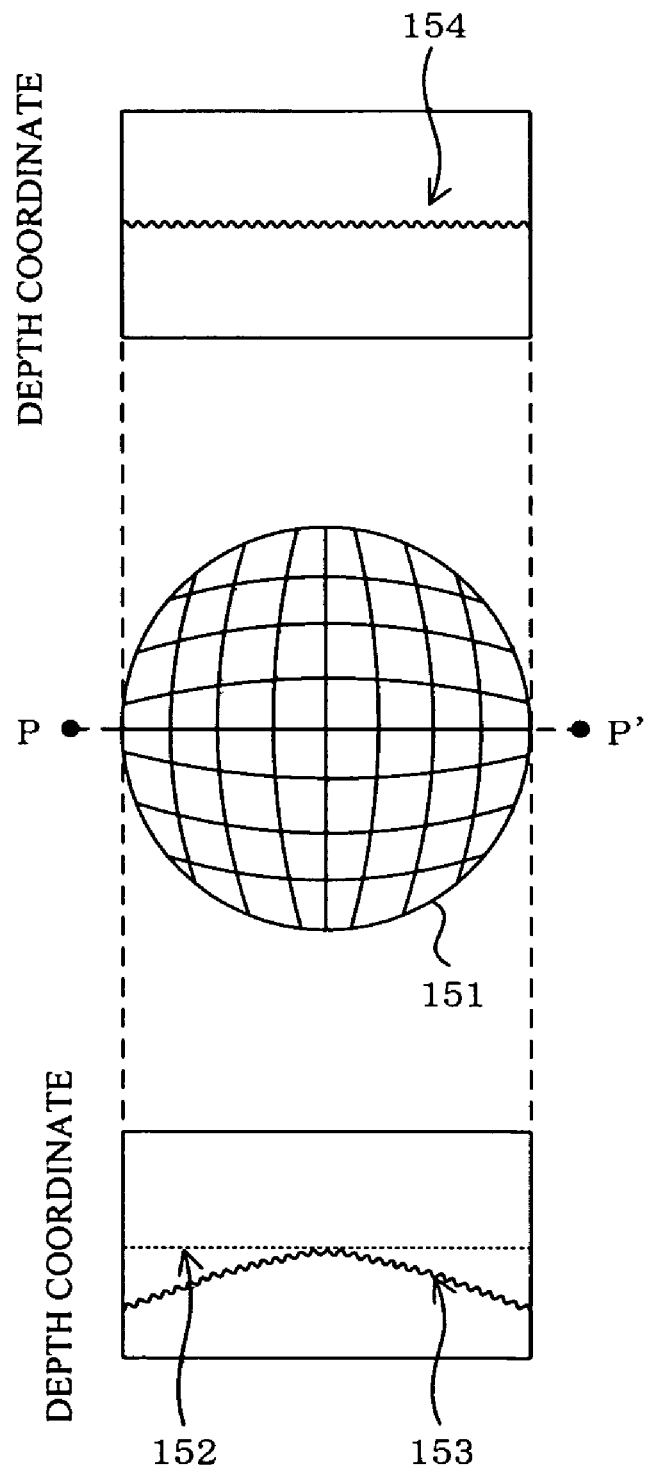
FIG. 5 is an illustrative view showing the problem of image distortion in stereo photography.

The photographic optical system of the fundus camera of FIG. 1, i.e., the objective lens 24 through the variable power lens 38a, has image distortion such as that shown in FIG. 5, and the left and right parallax images thus photographed are also affected in the manner described above.

Figure 3:
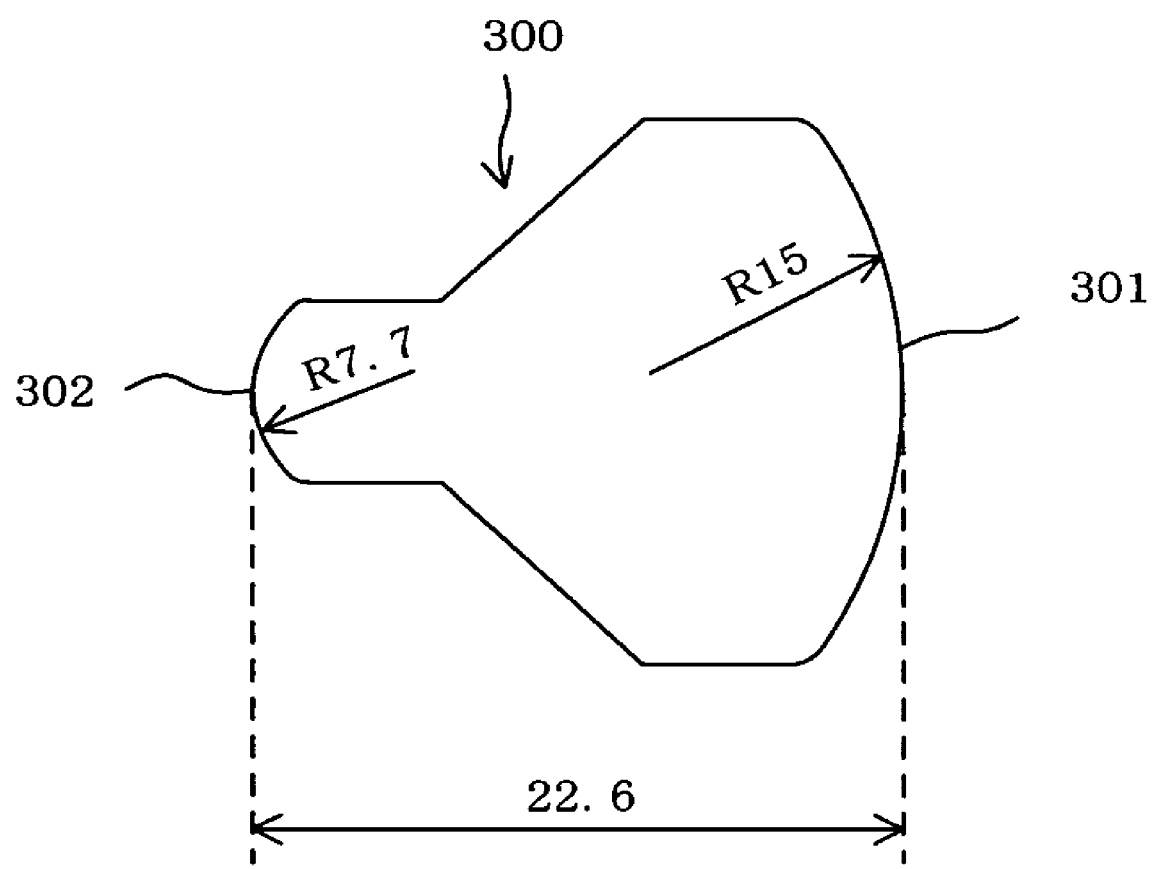
FIG. 3 is an illustrative view showing a model eye used in the apparatus of FIG. 1.

In view of this situation, in the present embodiment, a photographic target having a prescribed shape, i.e., a model eye 300 such as that shown in FIG. 3, is stereographically photographed in order to calculate inherent shape distortions in the optical system of the fundus camera and acquire calibration data that corresponds to the distortions and is capable of correcting the distortions.

The depth (length, or coordinate in the z-axis direction) as the three-dimensional measurement data obtained in the manner shown in FIGS. 6 to 8 is corrected based on the calibration data. The stereo image stereographically presented to the examiner on the stereo monitor 63 is also corrected using the same distortion data.

The model eye 300 is formed in a shape that models (simulates) the optical characteristics of a human eye such as that shown in FIG. 3. For example, the model eye 300 is fabricated by using methods such as cutting and polishing an optical glass having a refractive index of about n=1.52. The curvature of the cornea model surface (plane of incidence) 302 is about R 7.7 mm, and the curvature of the retina model surface 301 that corresponds to the retina is a spherical surface of about R 15 mm. The distance of these two surfaces is, e.g., about 22.6 mm.

With the calibration photography described hereinafter, an ocular fundus model surface for modeling the ocular fundus of the model eye 300 is photographed as a specific location for acquiring calibration data. More specifically, the ocular fundus model surface is configured as a surface 301 that models a retina in the model eye 300 of the present embodiment. The surface 301 that models the retina is worked as ground surface (semitransparent) and is provided with a grayscale pattern (e.g., a grid pattern or the like) by engraving and coloring, by printing, or by another method. A specific-pattern may be associated with a specific color so as to facilitate the process when the calibration data described hereinafter is produced.

The model eye 300 can be connected to and disconnected from the clamp mount 310 of the fundus camera of FIG. 1 (using, e.g., a latch coupling, threading, or another structure) by a one-touch operation via a jig 311 that has been calibrated to a prescribed shape as a mounting place, and it is convenient to use a configuration in which the model eye 300 is mounted in the optical system so as to be positioned in substantially the same position as the (ideal) position of the subject's eye E.

The calibration data for correcting the image data used in three-dimensional measurement can be acquired in the following manner using the model eye 300 described above at any time before or after the fundus camera of FIG. 1 has been shipped..

First, the model eye 300 is positioned in substantially the same position as the (ideal) position of the subject's eye E using a jig 311 such as described above, and the left and right parallax images are photographed in the manner described above.

The photographic distance and power are also brought to a fixed value for the calibration process. For this purpose, it is advantageous to provide a configuration in which a notch is made in the position of the optical system, for example, in the variable power ring (dial), or another component so that the photographic distance and power can be selected easily for the calibration process.

In the present example, the calibration data can be obtained by photographing the model eye 300 and calculating the three-dimensional shape in the manner described above. The calibration data is calculated for each variable power condition in the case that photography is carried out under different photographic power conditions using the variable lens 38a of the fundus camera.

Figure 10A:
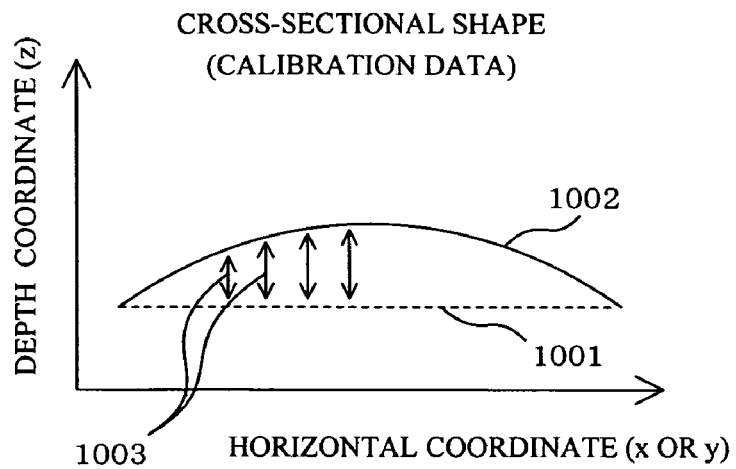
FIGS. 10a to 10c are an illustrative view showing a calibration process in the depth (z axis) direction in the apparatus of FIG. 1.

As shown in FIG. 10a, the calibration data corresponds to the difference 1003 between the shape 1001 of the actual model eye 300 and the three-dimensional shape (curve of the depth information (z coordinate)) 1002 obtained by photographing the model eye 300. A computational example of acquiring the difference 1003 will be described hereinafter.

In FIG. 10a, the three-dimensional shape 1002 obtained by photographing the model eye 300 is affected by image distortion, and the shape of the ocular fundus of the model eye 300 must essentially be obtained as shape 1001. In this case, the ocular fundus shape 1001 of the model eye 300 is shown to be substantially flat in order to facilitate the description.

The calibration data can be recorded as an expression of the difference 1003 in depths (coordinate in the z-axis direction) as shown in FIG. 10a, or as an expression of the difference in parallactic distances (it is apparent from Eq. (1) that depth is uniquely calculated as long as the parallactic distance is determined).

The calibration data thus calculated can be used to correct the three-dimensional shape of an ocular fundus obtained by actually photographing a subject's eye and obtaining the actual three-dimensional shape of the ocular fundus of the subject's eye.

Figure 10B:
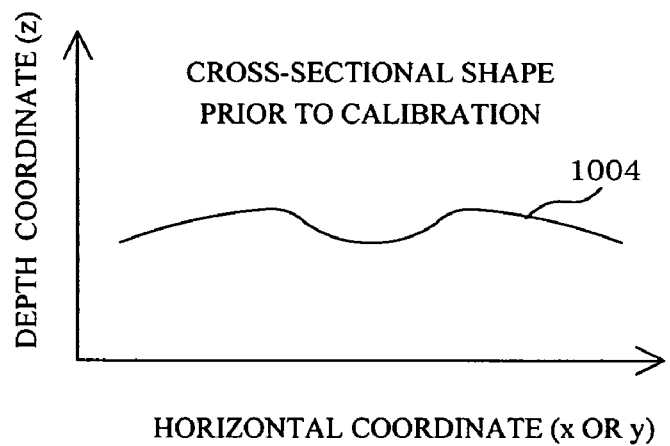
Figure 10C:
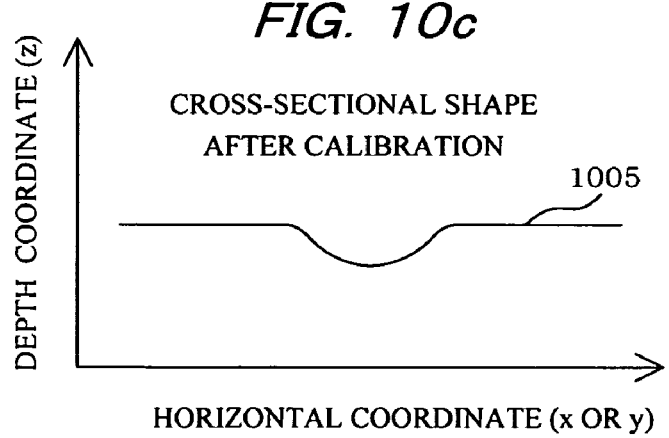

For example, a shape 1004 (curve of the depth information (z coordinate)) of the ocular fundus of the subject's eye is measured in the manner shown in FIG. 10b. The calibration data that expresses the difference 1003 is used to correct the shape 1004 to a shape 1005 of the ocular fundus of the subject's eye in the manner shown in FIG. 10c (in this case as well, the shape 1005 of the ocular fundus of the subject's eye is shown as being substantially flat in order to facilitate the description).

The calibration data calculated in the manner described above can be recording in a table format in an HDD, nonvolatile memory, or the like.

Calibration data that expresses depth (coordinate in the z-direction) is applied after the depth (coordinate in the z-direction) of the photographed image is calculated by the three-dimensional measurement process. Therefore, the calibration data is recorded in association with the horizontal coordinate (xy coordinate, or an expression of a polar coordinate from the center (optical axis) of the image) of the three-dimensional shape data. The calibration data is read and applied from the table by using the horizontal coordinate of the prescribed location within the ocular fundus shape data. The thus determined depth data (coordinate in the z-axis direction) is used to correct the depth of the actual location.

The calibration data is obtained as the parallactic distance at points of attention having a specific interval (about 4 pixels), for example. Therefore, the calibration data that expresses the parallactic distance is recorded in a table format for each point of attention. The table data is referenced based on the points of attention (point number and pixel address) being processed in the stage of the parallactic distance calculation (step S162) of FIG. 6, and the calibration data that expresses the parallactic distance can be read and applied in calculating the depth calculation (step S163).

Using calibration data in a table format such as that described above allows image distortions to be rapidly corrected by a very small computing load.

FIG. 9 shows the flow of the shape distortion correction and actual ocular fundus stereographic photography.

Shown in steps S901 and S902 of FIG. 9 are calibration photography and correction data acquisition that are carried out at any time before or after shipment of the fundus camera of FIG. 1.

In step S901, the model eye 300 is stereographically photographed in the manner described above, and in step S902, the calibration data is calculated in the manner described above.

In other words, in step S902, the parallactic distance is calculated from the left and right parallax images of the model eye 300 for each point of attention, and the shape data (1002 in FIG. 10a) of the model eye 300 is calculated. Since the ocular fundus shape (1001 in FIG. 10a) of the model eye 300 is known, the calibration data can be acquired as the difference (expressed as the depth or the parallactic distance) between the two shapes. The calibration data thus acquired is recorded in an HDD, nonvolatile memory, or the like in the manner described above.

Stereographic photography of an actual ocular fundus is then performed in step S161. Steps S161, S162', and S163' of FIG. 9 are substantially the same as the process of stereographic photography (S161), parallax pixel number measurement (S162), and depth calculation (S163) of FIG. 6. However, in FIG. 9, corrections are made in steps S162' and S163' using the calibration data recorded in a table format in the manner described above.

In other words, the calibration data that expresses parallactic distance is used to correct the parallax pixel number obtained in the measurement stage in step S162. Alternatively, the calibration data that expresses depth is used to correct the depth obtained in the depth calculation stage in step S163.

In this manner, shape distortion corrections that are unique to the optical system are applied for the left and right photographic images, thus allowing the parallax pixel number measurement and depth calculation of steps S162 and S163 to be accurately performed.

The same calibration data can be used in step S170 to correct stereo images that are stereographically viewed by an examiner on the stereo monitor 63. The 3D display of the stereo monitor 63 can be performed, e.g., concurrently with the calibration process by using the calibration data prepared as table data, rather than sequentially subsequent to the calibration process in the manner shown in FIG. 9 (steps S162' and S163').

Figure 11:
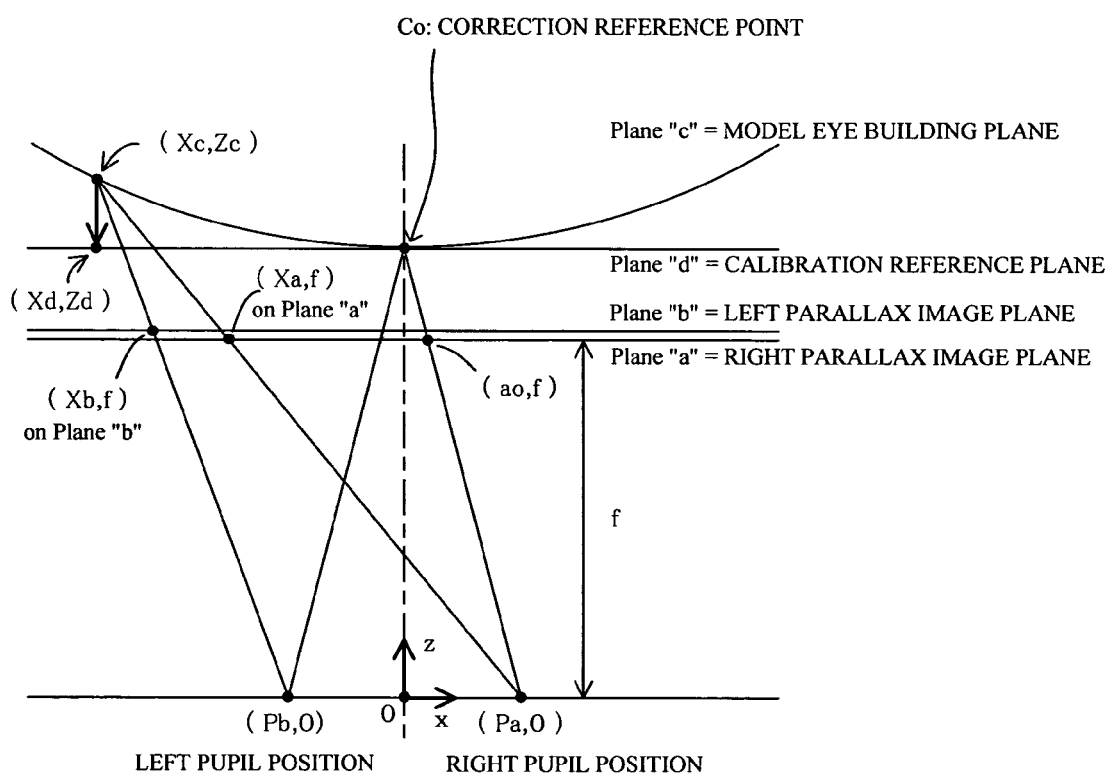
FIG. 11 is an illustrative view showing the calibration process of the stereo display image in the apparatus of FIG. 1.
Figure 12:
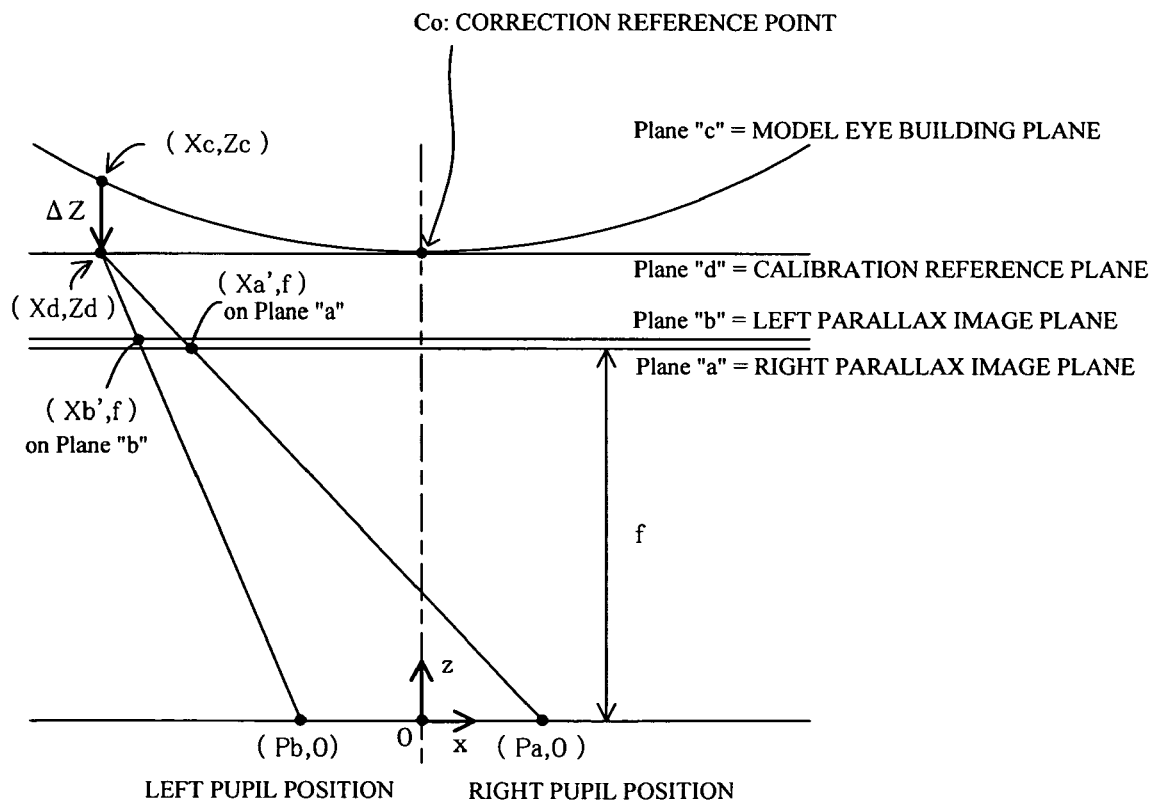
FIG. 12 is an illustrative view showing the calibration process of the stereo display image in the apparatus of FIG. 1.

FIGS. 11 and 12 show an overview of the process in which a 3D display image produced by the stereo monitor 63 is calibrated in step S170. In this case, the direction of depth calibration and the relationship with the z-axis direction is opposite of that in FIGS. 10a through 10c in order to facilitate description.

FIGS. 11 and 12 show the imaging relationship for a case in which the model eye 300 is photographed using the optical system of FIG. 1. In FIGS. 11 and 12, planes "a" and "b" correspond to the respective right and left parallax image planes captured by the CCD 41, and are shown at the positions on the object point side that are in the conjugate therewith. Here, planes "a" and "b" coincide with each other on a straight line but shown to be offset in the vertical direction in order to facilitate understanding of the diagram.

Plane "c" is a model eye-building plane, i.e., a three-dimensional shape of a model eye that has been built from the photography with a parallax in the optical system of FIG. 1 having distortions. The plane "c" is to be corrected to plane "d", which is a calibration reference plane that corresponds to the original shape of the model eye.

Here, in order to facilitate the description below, plane "d" i.e., the shape of the original model eye, is flat, and planes "c" and "d" match at the correction reference point C0 on the optical axis (matches the z-axis).

In other words, the diagram shows that the amount of correction in the direction of the x-, y-, and z-axes is 0 at the correction reference point C0. The pixels in the planes "a" and "b" are to be parallelly moved in a corresponding manner when a point on the coordinate on plane "c" other than the correction reference point C0 has moved to that on plane "d", e.g., when a point on the coordinate (Xc, Zc) has moved to a point on the coordinate (Xd, Zd).

The coordinate of the image formation point in the plane "a" at the correction reference point C0 is (a0, f).

The points (Pa, 0), (Pb, 0) are at the right and left pupil positions, and correspond to the conjugate positions of the stops 28a and 28b that are in conjugate with the anterior ocular segment (pupil) of a subject's eye, respectively. Also, the distance between the plane "a" or "b" (left and right parallax image plane) and the left or right pupil is made to match the ocular focal distance f of the subject's eye by the above-described setting of the photographic distance.

Correction of the images in planes "a" and "b" along the x-axis direction will be described using the xz plane, but the description below is also applicable to the yz plane by substituting x with y, and correction can also be carried out in the same manner in relation to the y-axis direction of the images in planes "a" and "b".

In this case, when the model eye 300 is photographed using the optical system of FIG. 1, plane "c" (model eye-building plane) of FIG. 11 is measured as the depth described above. The shape of plane "c" is computed as a shape in which the peripheral area is distant (concave) because the optical system of FIG. 1 includes distortions.

The points photographed as (Xa, f), (Xb, f) on planes "a" and "b" (left and right parallax image planes) determines a point (Xc, Zc) on plane "c" (model eye-building plane).

As described above, the difference Δz in depths is recorded, for example, as table data, whereby a process can be carried out to correct the point (Xc, Zc) to the point (Xd, Zd).

Here, the x coordinate value Xc and the z coordinate value Zc of the point (Xc, Zc) are calculated as follows using similar-triangles.

$$Xc = (Pa \cdot Xb - Pb \cdot Xa)/((Pa - Pb) - (Xa - Xb)) \quad (2)$$

$$Zc = f \cdot (Pa - Pb)/((Pa - Pb) - (Xa - Xb)) \quad (3)$$

Next, the point (Xc, Zc) is shifted in the z-axis direction in order to calculate the point (Xd, Zd) on the plane "d" (calibration reference plane). The x and y coordinate values Xd and Zd of the point (Xd, Zd) can be correlated using the following formulas, respectively.

$$Xd = Xc \quad (4)$$

$$Zd = f \cdot Pa/(Pa - a0) \quad (5)$$

The difference Δz in the depth can be calculated using the following formula.

$$\Delta z = Zd - Zc \quad (6)$$

Here, Zd and Zc use the values previously obtained in Eqs. (5) and (3). The Δz can also be stored in the table as the correction data described above.

The position of (Xa, f) and (Xb, f) on the planes "a" and "b" (left and right parallax image planes) shown in FIG. 11 must be corrected within the planes "a" and "b" in the manner shown in FIG. 12 in order to correct the 3D display image presented by the stereo monitor 63. In other words, the points (Xa, f) and (Xb, f) photographed on the planes "a" and "b" must be corrected to the positions (Xa', f) and (Xb', f) in FIG. 12 in order to set the point (Xd, Zd) on the plane "d" as a new building point.

The points (Xa', f) and (Xb', f) in FIG. 12 show the points that are obtained on planes "a" and "b" by photographing the corrected point (Xd, Zd), respectively.

In this case, the x coordinates Xa' and Xb' of the points (Xa', f) and (Xb', f) can be calculated using the following formulas.

$$Xa' = (Zd \cdot Pa - f \cdot Pa - f \cdot Xd)/(Zd - 2f) \quad (7)$$

$$Xb' = (Zd \cdot Pb - f \cdot Pb - f \cdot Xd)/(Zd - 2f) \quad (8)$$

If the point (Xc, Zc) is corrected to the point (Xd, Zd), where Xc=Xd, as mentioned above, i.e., if corrected in the depth direction (z-axis direction), the position of the corresponding points in the left and right parallax images of the planes "a" and "b" can be corrected in the x-axis direction. The position of the corresponding points can actually be corrected by moving the pixels in the left and right parallax images.

FIGS. 11 and 12 show the correction (calibration) in the x-axis direction in the xz plane. Correction (calibration) in the y-axis direction in the yz plane can be carried out in the same manner. Since such a procedure is laborious, the correction (calibration) in the y-axis direction in the yz plane has been omitted from the diagram. However, in such a case, if the notation related to the x coordinate in FIGS. 11 and 12 is substituted with a notation related to the y coordinate, the diagrammed processes would be the same as the correction (calibration) performed in the y-axis direction in the yz plane.

Thus, the correction image data is obtained in which the position of the corresponding points (pixels) in the left and right parallax images of the planes "a" and "b" has been corrected in the xy plane. The resulting correction image data can be displayed, recorded and output (e.g., printed), and transferred as data to an external storage apparatus or another processing apparatus (a computer or the like) as a database record.

For example, the left and right image data that has been corrected in the manner described above may be displayed in 3D on the stereo monitor 63. This may correct the view of the 3D display image on the monitor 63. In other words, the shape perceived by the examiner as the plane "c" of FIGS. 11 and 12 prior to correction may be calibrated so as to be perceived as plane "d" on a 3D display via the stereo monitor 63.

In the description of FIGS. 11 and 12, a computational example is shown for a case in which the plane "d" is (resembles) a flat plane that matches the plane "c" in the correction reference point C0. In this case, correction (calculation of Δz) of the depth direction from point (Xc, Zc) to (Xd, Zd) and correction of the parallax image are performed by simple geometric computation in the manner described above. However, it is also possible to use as an expression of the plane "d" the depth data (z-axis data) that is obtained by actually measuring the model eye in advance (or obtained from the design data of the model eye). In such a case, a point (Xd, Zd) on the plane "d" is made associated with a point (Xc, Zc) on the plane "c" that is built from the photographic data, wherein both the x coordinates coincide. It is apparent from Eqs. (7) and (8) that the point (Xd, Zd) is used to correct the coordinates of the pixels on the left and right parallax images that correspond to the point (Xc, Zc) (the same applies to the y-axis).

In the image processing apparatus of the present embodiment in which the ocular fundus of a subject's eye is thus stereographically photographed via a stereo photographic optical system and the resulting photographic image data is subjected to a three-dimensional measurement process, distortions in the optical system used in actual photography can be corrected, an accurate three-dimensional measurement process involving the ocular fundus image can be carried out, the stereo-shape of the ocular fundus of a subject's eye can be accurately evaluated, and misdiagnoses and other problems can be avoided.

Figure 4:
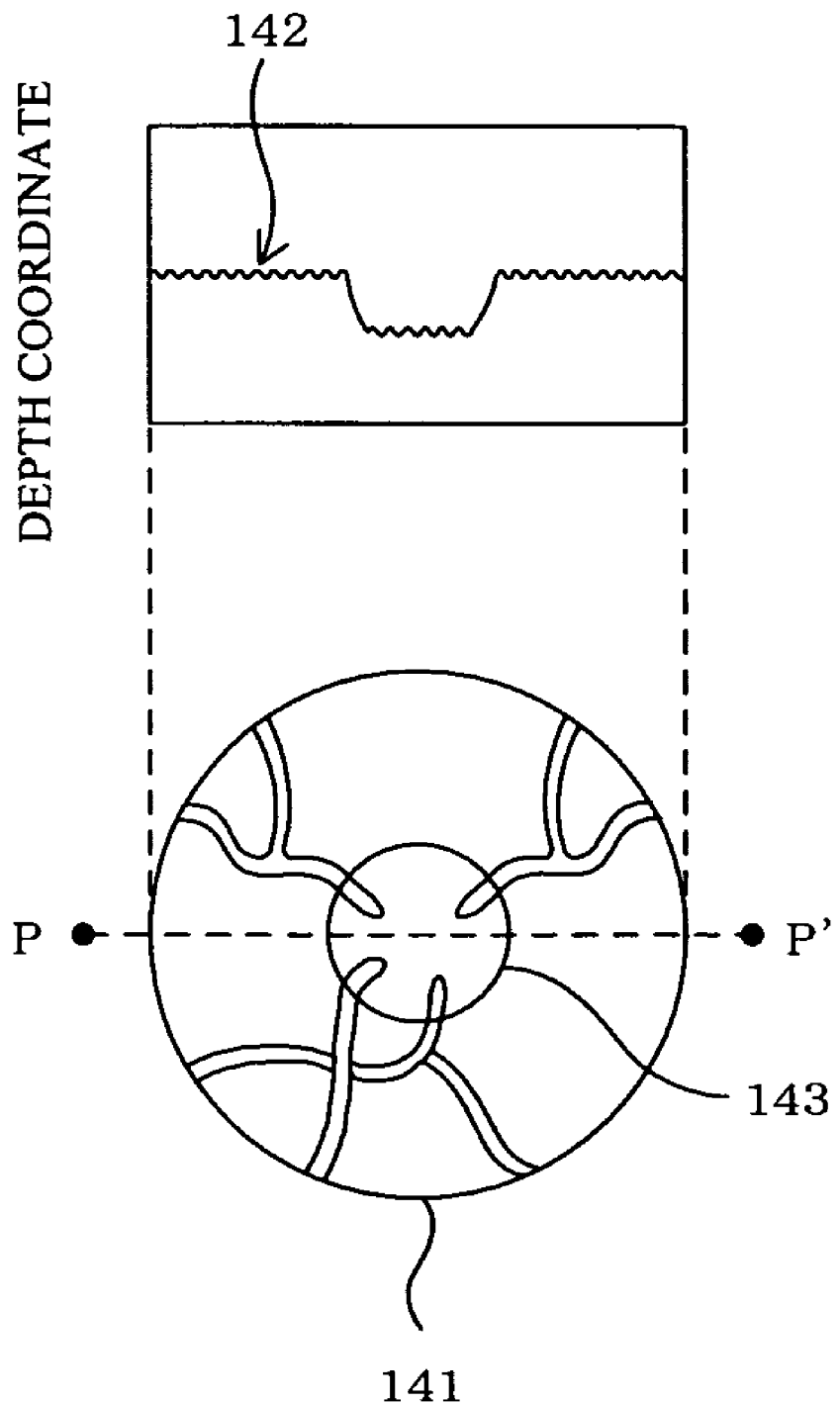
FIG. 4 is an illustrative view showing the result of measuring the stereo shape of an ocular fundus obtained in the apparatus of FIG. 1.

In the case of an ocular fundus image 141 such as that shown FIG. 4, for example, the stereo shape can be calculated as the depth information (z-axis coordinate value). It will be apparent that accurate consideration is given to the shape of the papillary portion 143 as shown by reference numeral 142 on the line P-P' by making corrections in the manner described above.

The present embodiment can provide a three-dimensionally measured accurate ocular fundus image that is free from distortions of the optical system and can be viewed by the examiner via a stereo monitor. The configuration (correction) process described above makes it possible to correct the images (left and right parallax images) for 3D display so that the examiner can observe (perceive) the shape of the ocular fundus of the subject's eye in accordance with a shape that has been corrected by the shape data. Therefore, the examiner can accurately evaluate the stereo shape of the ocular fundus of the subject's eye by perceiving the 3D display image.

As described above, the calibration process shown in FIGS. 11 and 12 is carried out along the x- and y-axes. This allows the shape in the xy plane of the 3D display image to be corrected. The correction process shown in FIGS. 11 and 12 is not limited to performing 3D display, and it is also advantageous even when only the left or right parallax image is used as an image to be measured.

Distortions in the image are unevenly generated on the left and right sides due to the fact that the left and right parallax images are photographed via stop apertures that are offset from the optical axis of the optical system. In principle, the calibration process shown in FIGS. 11 and 12 can correct image distortions that are uneven on the left and right sides, and thus form an image that is substantially equivalent to an image photographed via a stop on the optical axis, thereby providing an accurately measured ocular fundus image without distortions.

The calibration process of the present example can be easily carried out using calibration data obtained by photographing a model eye for modeling the shape and optical structure of a subject's eye. The calibration data can be recorded as a difference that is expressed as the depth or parallactic distance, can readily be used to correct the depth information (three-dimensional shape data) of the ocular fundus using a light computing load, and can be used to correct the ocular fundus image for display or for recording by using simple geometric computation such as that shown in FIGS. 11 and 12 using the same calibration data.

The photographic target that is stereo photographed for calculating the calibration data may theoretically be a photographic target such as graph paper. However, a model eye for modeling the shape and optical structure of the subject's eye is used in the manner of the embodiment described above. This enables calibration measurement and computation to be easily carried out without modifying other photographic and computational conditions.

An adapter or the like such as the jig 311 for mounting a model eye is provided, whereby calibration measurement and computation can be readily carried out, and the model eye, jig 311, model eye-mounting adapter, and other components can be supplied and sold as kits and expansion parts for calibration to users and maintenance workers.

The present invention can be applied to an image processing apparatus such as a fundus camera that stereographically photographs an ocular fundus of a subject's eye via a stereo photographic optical system, and carries out a three-dimensional measurement process involving the resulting photographic image data and/or displays/records the photographic image.

What is claimed is:

1. An image processing apparatus for stereographically photographing an ocular fundus of a subject's eye with a prescribed parallax via an ocular fundus photographic optical system and performing a three-dimensional shape measurement process using the resulting parallax image, the apparatus comprising:
   means for stereographically photographing a photographic target having a prescribed shape with a prescribed parallax via the ocular fundus photographic optical system;
   means for measuring the three-dimensional shape of a prescribed location of said target on the basis of image data derived from the parallax image thereof; and
   means for producing calibration data for correcting shape distortions caused by the ocular fundus photographic optical system, the calibration data corresponding to a difference between an actual three-dimensional shape of the prescribed location of said target and a three-dimensional shape of the prescribed location thereof that has been measured based on the image data;
   wherein the calibration data is used in the three-dimensional shape measurement process for shape distortion correction for a three-dimensional shape data obtained by stereo photography of the ocular fundus of the subject's eye.

2. An image processing apparatus according to claim 1, wherein the parallax image data obtained by stereo photography of the ocular fundus of the subject's eye is subjected to shape distortion correction based on the calibration data to produce shape distortion-corrected parallax image data of the ocular fundus of the subject's eye.

3. An image processing apparatus according to claim 1, wherein the photographic target is a model eye that simulates the shape and optical characteristics of a human eye and has as the prescribed location an ocular fundus model surface endowed with a prescribed grayscale pattern.

4. An image processing apparatus according to claim 1, wherein the calibration data is expressed by a parallactic distance that is to be corrected in the three-dimensional shape measurement process.

5. An image processing apparatus according to claim 1, wherein the calibration data is expressed by a depth that is to be corrected in-the three-dimensional shape measurement process.

6. An image processing apparatus according to claim 1, wherein the calibration data is produced for each variable power condition of the ocular fundus photographic optical system.

7. An image processing apparatus according to claim 1, wherein the calibration data is produced in a table format in association with a horizontal coordinate of three-dimensional shape data or a specific location in the parallax image stereographically photographed by the ocular fundus photographic optical system.

8. An image processing apparatus according to claim 3, further comprising a mounting place for positioning the model eye in substantially the same position as the position of the subject's eye in the ocular fundus photographic optical system.

9. An image processing apparatus for stereographically photographing an ocular fundus of a subject's eye with a prescribed parallax via an ocular fundus photographic optical system and performing a three-dimensional shape measurement process using the resulting parallax image, the apparatus comprising:

means for stereographically photographing a photographic target having a prescribed shape with a prescribed parallax via the ocular fundus photographic optical system;

means for measuring the three-dimensional shape of a prescribed location of said target on the basis of image data derived from the parallax image thereof; and means for producing calibration data for correcting shape distortions caused by the ocular fundus photographic optical system, the calibration data corresponding to a difference between an actual three-dimensional shape of the prescribed location of said target and a three-dimensional shape of the prescribed location thereof that has been measured based on the image data;

wherein the parallax image data obtained by stereo photography of the ocular fundus of the subject's eye is subjected to shape distortion correction based on the calibration data to produce shape distortion-corrected parallax image data of the ocular fundus of the subject's eye.

10. An image processing apparatus according to claim 9, wherein left and right parallax image data is subjected to shape distortion correction based on the calibration data to produce left and right shape distortion-corrected parallax image data for stereo display on a stereo monitor.

11. An image processing apparatus according to claim 9, wherein the calibration data is expressed by a depth that is to be corrected in the three-dimensional shape measurement process, and the parallax image data is subjected to shape distortion correction using geometric computation based on the calibration data to produce the shape distortion-corrected parallax image data of the ocular fundus of the subject's eye.

12. An image processing apparatus according to claim 9, wherein the photographic target is a model eye that simulates the shape and optical characteristics of a human eye and has as the prescribed location an ocular fundus model surface endowed with a prescribed grayscale pattern.

13. An image processing apparatus according to claim 9, wherein the calibration data is expressed by a parallactic distance that is to be corrected in the three-dimensional shape measurement process.

14. An image processing apparatus according to claim 9, wherein the calibration data is expressed by a depth that is to be corrected in the three-dimensional shape measurement process.

15. An image processing apparatus according to claim 9, wherein the calibration data is produced for each variable power condition of the ocular fundus photographic optical system.

16. An image processing apparatus according to claim 9, wherein the calibration data is produced in a table format in association with a horizontal coordinate of three-dimensional shape data or a specific location in the parallax image stereographically photographed by the ocular fundus photographic optical system.

17. An image processing apparatus according to claim 12, further comprising a mounting place for positioning the model eye in substantially the same position as the position of the subject's eye in the ocular fundus photographic optical system.

* * * * *